US009155633B2

(12) United States Patent
Cloutier et al.

(10) Patent No.: US 9,155,633 B2
(45) Date of Patent: Oct. 13, 2015

(54) METHOD AND SYSTEM FOR PERFORMING SPINAL SURGICAL PROCEDURES USING NATURAL ORIFICES

(71) Applicant: NovApproach Spine LLC, Alachua, FL (US)

(72) Inventors: Raymond J. Cloutier, Alachua, FL (US); Larry G. Hickey, Alachua, FL (US)

(73) Assignee: NovApproach, Spine LLC, Alachua, FL (US)

( * ) Notice: Subject to any disclaimer, the term of this patent is extended or adjusted under 35 U.S.C. 154(b) by 0 days.

(21) Appl. No.: 14/618,347

(22) Filed: Feb. 10, 2015

(65) Prior Publication Data
US 2015/0209157 A1 Jul. 30, 2015

Related U.S. Application Data

(63) Continuation of application No. 13/678,248, filed on Nov. 15, 2012, now Pat. No. 8,979,861.

(60) Provisional application No. 61/561,041, filed on Nov. 17, 2011.

(51) Int. Cl.
A61F 2/46 (2006.01)
A61B 17/02 (2006.01)
(Continued)

(52) U.S. Cl.
CPC ........... A61F 2/4611 (2013.01); A61B 17/0218 (2013.01); A61B 17/320016 (2013.01); A61B 17/7074 (2013.01); A61F 2/4455 (2013.01); A61B 17/3421 (2013.01);
(Continued)

(58) Field of Classification Search
CPC ........... A61B 17/3421; A61B 17/7074; A61B 17/1671
See application file for complete search history.

(56) References Cited

U.S. PATENT DOCUMENTS 5,334,183 A 8/1994 Wuchinich
6,096,046 A 8/2000 Weiss
(Continued)

FOREIGN PATENT DOCUMENTS

WO 2011041668 4/2011

OTHER PUBLICATIONS

Schlenzka, D., Laine, T., & Lund, T. (2000). Computer-assisted spine surgery. European Spine Journal, 9(1), S057-S064.
(Continued)

Primary Examiner — Andrew Yang
(74) Attorney, Agent, or Firm — Meyertons, Hood, Kivlin, Kowert & Goetzel, P.C.; Eric B. Meyertons

(57) ABSTRACT

This disclosure describes devices and methods for performing spinal surgical procedures. In some embodiments, a method may include positioning at least a portion of at least one surgical instrument in at least one naturally occurring orifice of a human by a user. In some embodiments, a method may include accessing an interior space of the human using at least one of the surgical instruments. The method may include performing at least a portion of a spinal surgical procedure using at least one of the surgical instruments positioned in at least one of the naturally occurring orifices of the human. The method may include removing at least one of the surgical instruments from at least one of the naturally occurring orifices upon completion of at least a portion of the spinal surgical procedure.

20 Claims, 5 Drawing Sheets

(51) Int. Cl.
*A61B 17/32* (2006.01)
*A61B 17/70* (2006.01)
*A61F 2/44* (2006.01)
*A61B 17/00* (2006.01)
*A61B 17/34* (2006.01)

(52) U.S. Cl.
CPC .............. *A61B 2017/00238* (2013.01); *A61B 2017/00296* (2013.01); *A61B 2017/00318* (2013.01)

(56) References Cited

U.S. PATENT DOCUMENTS

| | | | |
|---|---|---|---|
| 6,328,730 | B1 | 12/2001 | Harkrider, Jr. |
| 8,568,306 | B2 | 10/2013 | Hardenbrook |
| 8,702,702 | B1 | 4/2014 | Edwards et al. |
| 8,771,170 | B2 | 7/2014 | Mesallum et al. |
| 2007/0233118 | A1 | 10/2007 | McLain |
| 2010/0286473 | A1 | 11/2010 | Roberts |
| 2011/0082370 | A1 | 4/2011 | Ducharme et al. |
| 2013/0197644 | A1 | 8/2013 | Cloutier |
| 2013/0345704 | A1 | 12/2013 | Palmer et al. |

OTHER PUBLICATIONS

Lee, J. Y., Lega, B., Bhowmick, D., Newman, J. G., Weinstein, G. S., Grady, M. S., & Welch, W. C. (2010). Da Vinci Robot-assisted transoral odontoidectomy for basilar invagination. ORL, 72(2), 91.
Onders, R., McGee, M. F., Marks, J., Chak, A., Schilz, R., Rosen, M. J., . . . & Ponsky, J. (2007). Diaphragm pacing with natural orifice transluminal endoscopic surgery: potential for difficult-to-wean intensive care unit patients. Surgical endoscopy, 21(3), 475-479.
Laufer, I., Greenfield, J. P., Anand, V. K., Hall, R., & Schwartz, T. H. (2008). Endonasal endoscopic resection of the odontoid process in a nonachondroplastic dwarf with juvenile rheumatoid arthritis: feasibility of the approach and utility of the intraoperative Iso-C three-dimensional navigation. J Neurosurg Spine 8:376-380, 2008.
Regan, J. J., & Guyer, R. D. (1997). Endoscopic Techniques in Spinal Surgery. Clinical Orthopaedics and Related Research, 335, 122-139.
Lee, A., Sommer, D., Reddy, K., Murty, N., & Gunnarsson, T. (2010). Endoscopic transnasal approach to the craniocervical junction. Skull Base,20(3), 199.
Form 10-K, Intuitive Surgical. Filed Feb. 6, 2009. See p. 12 for statement about "abdominal Sacral Colpopexy" a gynecological surgical procedure.
Form 10-K, Intuitive Surgical. Filed Jan. 29, 2010. See p. 13 for statement about "Transoral" Otolaryngologic surgery.
Regan, J. J., Yuan, H., & McAfee, P. C. (1999). Laparoscopic fusion of the lumbar spine: minimally invasive spine surgery: a prospective multicenter study evaluating open and laparoscopic lumbar fusion. Spine, 24(4), 402-411.
Magno, P., Khashab, M. A., Mas, M., Giday, S. A., Buscaglia, J. M., Shin, E. J., . . . & Kalloo, A. N. (2012). Natural orifice translumenal endoscopic surgery for anterior spinal procedures. Minimally invasive surgery, 2012.
Makris, K. I., Rieder, E., & Swanstrom, L. L. (Feb. 2010). Natural orifice trans-luminal endoscopic surgery (NOTES) in thoracic surgery. In Seminars in thoracic and cardiovascular surgery (vol. 22, No. 4, pp. 302-309). WB Saunders.
Magno, P., Rivera, Y., Buscaglia, J. M., Shin, E. J., Kantsevoy, S. V., Dray, X., & Kalloo, A. N. (2008). NOTES is successful for vertebral spinal interventions with significant advantages for anterior spinal procedures. Gastrointestinal Endoscopy, 67(5), AB114.
Yang, M. S., Kim, K. N., Kim, H., Yang, J. W., Yi, S., Lee, J. Y., . . . & Ha, Y. (2011). Robot-assisted anterior lumbar interbody fusion in a Swine model in vivo test of the da vinci surgical-assisted spinal surgery system. Spine, 36(2), E139-E143.
Yang, M. S., Yoon, T. H., Yoon, D. H., Kim, K. N., Pennant, W., & Ha, Y. (2011). Robot-assisted transoral odontoidectomy: experiment in new minimally invasive technology, a cadaveric study. Journal of Korean Neurosurgical Society, 49(4), 248-251.
Inoue, H., Takeshita, K., & Endo, M. (1994). Single-port laparoscopy assisted appendectomy under local pneumoperitoneum condition. Surgical endoscopy,8(6), 714-716.
Hadley, M. N., Spetzler, R. F., & Sonntag, V. K. (1989). The transoral approach to the superior cervical spine: a review of 53 cases of extradural cervicomedullary compression. Journal of neurosurgery, 71(1), 16-23.
Tong, F. C., Cloft, H. J., Joseph, G. J., Rodts, G. R., & Dion, J. E. (2000). Transoral approach to cervical vertebroplasty for multiple myeloma. American Journal of Roentgenology, 175(5), 1322-1324.
Merwin, G. E., Post, J. C., & Sypert, G. W. (1991). Transoral approach to the upper cervical spine. The Laryngoscope, 101(7), 780-784.
Rock, J. P., Tomecek, F. J., & Ross, L. (1993). Transoral surgery: an anatomic study. Skull base surgery, 3(3), 109.
Marotta, N. et al. "A novel minimally invasive presacral approach and instrumentation technique for anterior L5-S1 intervertebral discectomy and fusion" Neurosurg. Focus, vol. 20, Jan. 2006.
Khashab, M. et al. "Critical analysis of hot topics in NOTES" Nat. Rev. Gastroenterol. Hepatol. 8, 565-572 (2011).
Program for 6th International Conference on NOTES at InterContinental Chicago O'Hare in Chicago, Illinois, USA, Jul. 7-9, 2011.
Roberts, K. E. "An Insider's Note on NOTES: The Dawn of Prime Time" Medscape General Surgery, WebMD LLC, Posted Jun. 14, 2011.
Non-Final Office Action for U.S. Appl. No. 13/678,248 mailed on Jul. 7, 2014.
Notice of Allowance for U.S. Appl. No. 13/678,248 mailed on Nov. 21, 2014.
Issue Notification for U.S. Appl. No. 13/678,248 mailed on Feb. 26, 2015.
Magno, P. et al. "Natural Orifice Translumenal Endoscopic Surgery for Anterior Spinal Procedures" Minimally Invasive Surgery, vol. 2012, Article ID 365814, 6 pages.
Magno, P. et al. "NOTES is Successful for Vertebral Spinal Interventions with Significant Advantages for Anterior Spinal Procedures" Gastrointestinal Endoscopy, vol. 67, No. 5 : 2008.

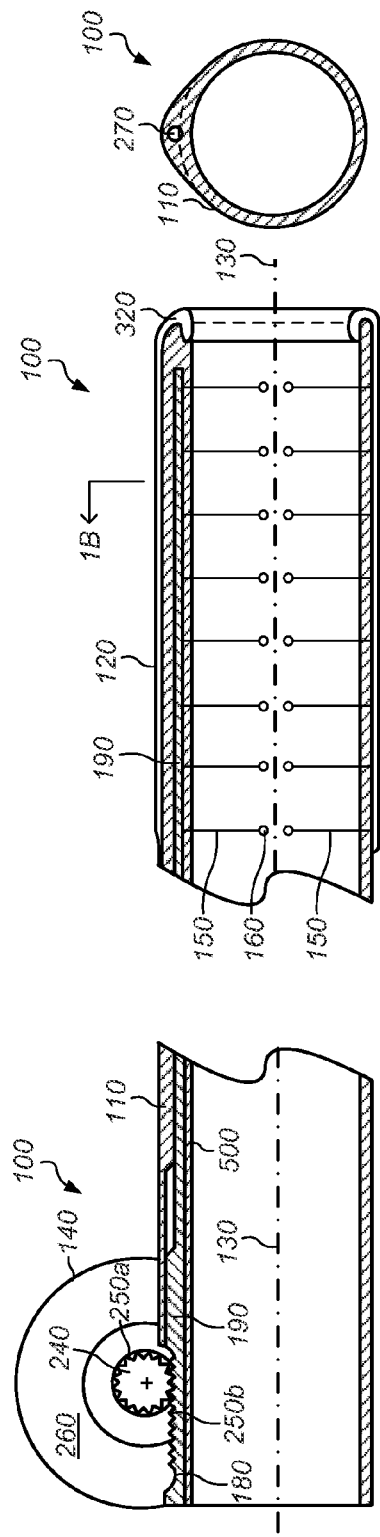
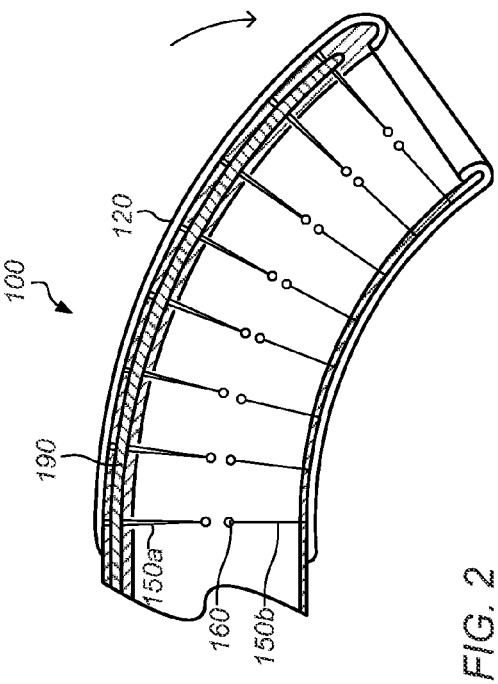
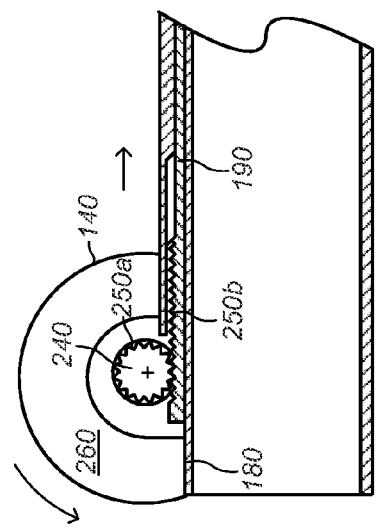
FIG. 1A
FIG. 1B
FIG. 2

METHOD AND SYSTEM FOR PERFORMING SPINAL SURGICAL PROCEDURES USING NATURAL ORIFICES

PRIORITY CLAIM

This application is a continuation of U.S. patent application Ser. No. 13/678,248 entitled "A METHOD AND SYSTEM FOR PERFORMING SPINAL SURGICAL PROCEDURES USING NATURAL ORIFICES" filed on Nov. 15, 2012, which claims priority to U.S. Provisional Patent Application No. 61/561,041 entitled "A METHOD AND SYSTEM FOR PERFORMING SPINAL SURGICAL PROCEDURES USING NATURAL ORIFICES" filed on Nov. 17, 2011, which is incorporated by reference herein.

BACKGROUND OF THE INVENTION

1. Field of the Invention

The present disclosure generally relates to methods and devices for performing spinal surgical procedures. More particularly, the disclosure generally relates to methods and devices for performing spinal surgical procedures by accessing a spinal column endoscopically through a naturally occurring orifice.

2. Description of the Relevant Art

Minimal invasive surgery ("MIS") has several benefits over more traditional surgical techniques. Benefits include a lower rate of morbidity, reduced pain, reduced scarring, reduced blood loss and reduced recovery time and costs.

In minimal invasive surgery, small incisions, typically about 0.5 to about 1.5 centimeters in length, are made in, for example, the abdominal wall (procedures restricted to the abdomen are referred to as laparoscopic surgery) for the insertion of trocar ports (or other surgical instruments). Trocar ports are thin tubes which allow for visualization of an internal cavity of the human body, as well as, for the insertion and extraction of the surgical instruments required to perform the surgery.

In order to perform, for example laparoscopic surgery, the abdominal wall is pressurized with a gas (e.g., carbon dioxide). The abdominal wall is pressurized to a pressure of between about 10 and about 20 mm Hg. Pressurizing the abdominal wall creates a working space between the internal organs and the peritoneum. One of the most commonly employed surgical instruments is an endoscope, usually including a light source and imaging system. The endoscope sends video images to a monitor. The images allow surgeons and medical staff to monitor the introduction of surgical instruments such that the surgical instruments are introduced with no or minimal damage to the surrounding tissue.

A further extension of minimally invasive surgery that is being developed currently involves using naturally occurring orifices to access internal cavities and organs within subjects. Natural orifice transluminal endoscopic surgery ("NOTES") uses natural orifices to access, for example, the abdomen, obviously has even greater benefits in that at least one fewer artificially created surgical opening is required to conduct a minimally invasive surgery, and thus reduced trauma to the subject. Naturally occurring orifices which have been tested and/or postulated for NOTES procedures include vaginal, rectal, and/or esophageal orifices.

United States Publication No. 20100286473 issued to Roberts (hereinafter "Roberts") discloses a device that can be delivered into a body cavity to manipulate tissue intracorporeally while being controlled extracorporeally and a method of using the device to perform a single-port laparoscopic or natural orifice surgery. However, Roberts does not disclose a method and/or device capable of performing a spinal fusion through a natural orifice.

Khashab et al. "Critical analysis of hot topics in NOTES" Nature Reviews: Gastroenterology & Hepatology Volume 8, October 2011, pages 565-572 (hereinafter "Khashab") discloses a review and analysis of the state of the art as it relates to natural orifice transluminal endoscopic surgery. However, Khashab does not disclose a method and/or device capable of performing a spinal fusion through a natural orifice.

What is needed is an improved device and/or method for performing spinal surgical procedures (e.g., spinal fusions) using one or more natural orifices.

SUMMARY

This disclosure describes devices and methods for performing spinal surgical procedures. In some embodiments, a method may include positioning at least a portion of at least one surgical instrument in at least one naturally occurring orifice of a human by a user. In some embodiments, a method may include accessing an interior space of the human using at least one of the surgical instruments. The method may include performing at least a portion of a spinal surgical procedure using at least one of the surgical instruments positioned in at least one of the naturally occurring orifices of the human. In some embodiments, the method may include removing at least one of the surgical instruments from at least one of the naturally occurring orifices upon completion of at least a portion of the spinal surgical procedure.

In some embodiments, a method may include positioning at least a distal end of a first shaft in at least one naturally occurring orifice. At least a portion of at least one of the surgical instruments may be positioned in the first shaft during use. The method may include observing a surgical site in the subject using an imaging device and a light source coupled to the first shaft. In some embodiments, the method may include conveying a fluid through a second shaft to a surgical site. The fluid may include saline. The second shaft may be coupled to the first shaft. The method may include conveying a fluid through a third shaft from a surgical site. The third shaft may be coupled to the first shaft.

In some embodiments, at least a distal end of the first shaft is flexible. The distal end of the first shaft may be flexible to accommodate positioning at least a portion of the surgical instrument adjacent a surgical site in the subject. At least a portion of the first shaft may be formed from stainless steel or other surgical grade material. In some embodiments, at least a portion of the distal end of the first shaft may include slits cut through the first shaft from an edge of the channel towards the center of the first shaft such that the distal end of the first shaft is flexible.

In some embodiments, a first shaft may include an elastomeric outer sheath. In some embodiments, a first shaft may include an elastomeric inner sheath.

In some embodiments, a method may include securing a position of at least the distal end of the first shaft adjacent the surgical site in the subject relative to the surgical site.

In some embodiments, at least one of the naturally occurring orifices may include an umbilical orifice. In some embodiments, at least one of the naturally occurring orifices may include a vaginal orifice. In some embodiments, at least one of the naturally occurring orifices may include a rectal orifice. In some embodiments, at least one of the naturally occurring orifices may include an esophageal orifice. In some embodiments, at least one of the naturally occurring orifices may include a nasal orifice.

In some embodiments, at least one of the surgical instruments may include a flexible portion. In some embodiments, at least one of the surgical instruments may include a pituitary rongeur, a Kerrison rongeur, an osteotome, or a curette.

In some embodiments, at least one of the surgical instruments comprises a flexible portion to accommodate positioning at least a portion of the surgical instrument in at least one of the naturally occurring orifices.

In some embodiments, a spinal surgical procedure may include a fusion procedure. In some embodiments, a spinal surgical procedure may include a vertebralplasty procedure or a kyphoplasty procedure. A spinal surgical procedure may include coupling plates, screws, and/or rods to at least a portion of a spinal column. A spinal surgical procedure may include positioning interbody devices, vertebral body replacement devices, disc replacement devices, nucleus devices, allografts, synthetic biological tissues (e.g., HATCP) or allograft tissue. A spinal surgical procedure may include administering pharmaceuticals.

In some embodiments, a spinal surgical procedure may include a disc herniation repair procedure. A disc herniation repair procedure may include localizing a herniation; excising at least a portion of an expulsed disc material; and repairing the annulus.

In some embodiments, a spinal surgical procedure may include an anterior interbody fusion procedure. The spinal surgical procedure may include retracting tissue such that an intervertebral disc is more accessible. At least a portion of the spinal surgical procedure may include a discectomy. At least a portion of the spinal surgical procedure may include a discectomy such that at least a portion of an intervertebral disc is removed. At least a portion of the spinal surgical procedure may include distracting at least two vertebrae. At least a portion of the spinal surgical procedure may include distracting at least two vertebrae to increase a distance between at least two of the vertebrae. At least a portion of the spinal surgical procedure may include sizing an implant device. At least a portion of the spinal surgical procedure may include implanting an interbody device. The interbody device may include an expandable interbody device. The expandable interbody device may include at least two portions which are assembled in the subject. At least two portions may be assembled in the subject such that the portions are smaller than the assembled expandable interbody device and, as such, easier to convey through the naturally occurring orifice of the subject.

In some embodiments, at least one of the naturally occurring orifices may include a vaginal orifice, and wherein the spinal surgical procedure includes an anterior interbody fusion procedure.

In some embodiments, a device and/or system is disclosed for performing the methods described herein.

In some embodiments, a device for assisting in the performance of a natural orifice transluminal spinal surgical procedure may include a first shaft. A distal end of the first shaft may be positionable, during use, in at least one naturally occurring orifice. The distal end of the first shaft may flexible to accommodate positioning the distal end of the first shaft adjacent a surgical site in the subject.

In some embodiments, the first shaft may include first set of slits cut through the first shaft from a first edge of the first shaft towards a center of the first shaft. The first shaft may include a second set of slits cut through the first shaft from a second edge of the first shaft towards the center of the first shaft. The second edge may be positioned substantially opposite the first edge. The first and the second set of slits may open and/or close in coordination to allow the flexible distal end to bend. The first and the second set of slits may open and/or close in coordination to allow the flexible distal end to bend within limitations determined by the dimensions and position of the first set of slits relative to the second set of slits.

In some embodiments, a device for assisting in the performance of a natural orifice transluminal spinal surgical procedure may include at least one surgical instrument. At least a portion of at least one of the surgical instruments may be positionable, during use, in the first shaft.

In some embodiments, a method for performing a natural orifice transluminal anterior interbody fusion procedure may include positioning at least a portion of a distal end of a surgical instrument in at least one naturally occurring orifice of a subject by a user. The surgical instrument may include a shaft. The method may include bending at least a portion of a distal end of the shaft. In some embodiments, the method may include bending at least a portion of a distal end of the shaft such that the distal end of the shaft is substantially adjacent an intervertebral disc to be removed. In some embodiments, the method may include implanting an intervertebral implant within an intervertebral space between endplates of adjacent vertebra.

In some embodiments, a method of implanting the intervertebral implant may include inserting an upper member, through the shaft, into the intervertebral space such that a superior surface of the upper member contacts an endplate of an upper one of the adjacent vertebra. The method of implanting the implant may include inserting a lower member, through the shaft, into the intervertebral space such that an inferior surface of the lower member contacts an endplate of a lower one of the adjacent vertebra. The method of implanting the implant may include inserting, through the shaft, an insert between the upper and lower members.

BRIEF DESCRIPTION OF THE DRAWINGS

Advantages of the present invention may become apparent to those skilled in the art with the benefit of the following detailed description of the preferred embodiments and upon reference to the accompanying drawings.

FIGS. 1A-B depict a representation of an embodiment of portions of a device, including a cross-section of a portion of the device, for performing a natural orifice surgical procedure wherein the distal end is substantially straight.

FIG. 2 depicts a representation of an embodiment of portions of a device for performing a natural orifice surgical procedure wherein a flexible distal end is bent at an angle.

Figure 3:
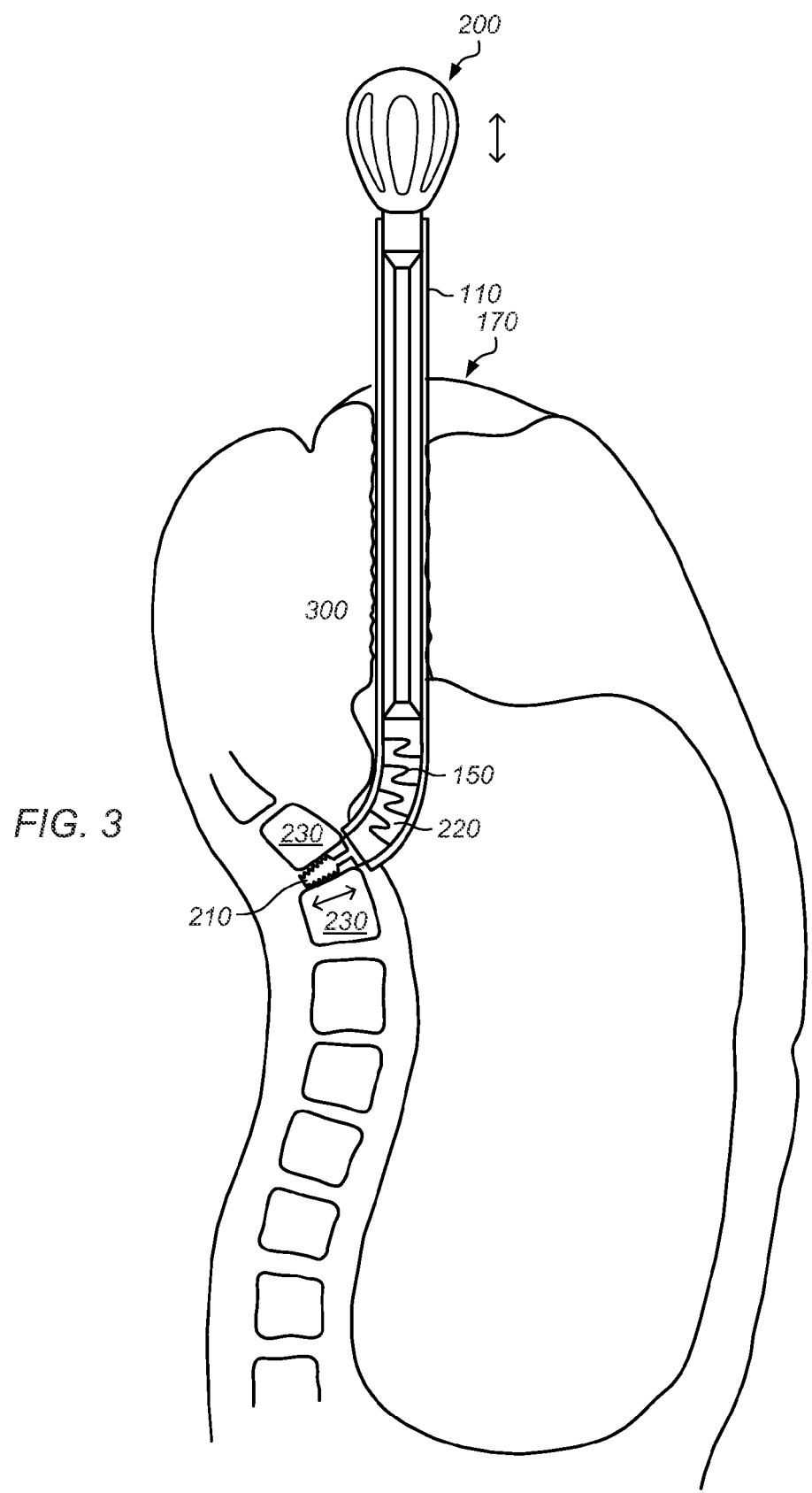
FIG. 3 depicts a representation of an embodiment of a device for performing a natural orifice transluminal discectomy, a distal end of which is positioned in a natural orifice during a transvaginal procedure.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DEFINITIONS

Unless defined otherwise, all technical and scientific terms used herein have the same meaning as commonly understood by one of ordinary skill in the art.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

The phrase "naturally occurring orifice" as used herein generally refers to any opening in a subject which occurs naturally (i.e., not created by a surgeon) including, but not limited to, an umbilical orifice, a vaginal orifice, a rectal orifice, an esophageal orifice, or a nasal orifice.

A type of minimally invasive surgery that is being developed currently involves using naturally occurring orifices to access internal cavities and organs within subjects. Natural orifice transluminal endoscopic surgery ("NOTES") uses natural orifices to access, for example, the abdomen. This obviously has even greater benefits in that at least one fewer artificially created surgical opening is required to conduct a minimally invasive surgery, and thus reduced trauma to the subject. A further practical consequence and advantage of using NOTES is that fewer surgeons may be required to perform the actual procedure. Currently an access surgeon is needed during certain surgical procedures in order to assist a primary surgeon tasked with conducting the actual procedure.

This disclosure describes devices and methods for performing spinal surgical procedures. In some embodiments, a method may include positioning at least a portion of at least one surgical instrument in at least one naturally occurring orifice of a human by a user. In some embodiments, a method may include accessing an interior space of the human using at least one of the surgical instruments. The method may include performing at least a portion of a spinal surgical procedure using at least one of the surgical instruments positioned in at least one of the naturally occurring orifices of the human. In some embodiments, the method may include removing at least one of the surgical instruments from at least one of the naturally occurring orifices upon completion of at least a portion of the spinal surgical procedure.

In some embodiments, at least one of the naturally occurring orifices may include an umbilical orifice. In some embodiments, at least one of the naturally occurring orifices may include a vaginal orifice. In some embodiments, at least one of the naturally occurring orifices may include a rectal orifice. In some embodiments, at least one of the naturally occurring orifices may include an esophageal orifice. In some embodiments, at least one of the naturally occurring orifices may include a nasal orifice.

FIGS. 1-6 depict a representation of embodiments of a device for performing a natural orifice surgical procedure. In some embodiments, a method may include positioning at least a distal end of a first shaft in at least one naturally occurring orifice. The first shaft may be part of an endoscope. At least a portion of at least one of the surgical instruments may be positioned in the first shaft during use. In some embodiments, at least one of the surgical instruments may be formed as a permanent part of the first shaft. In some embodiments, surgical instruments may be positionable in the first shaft such that different surgical instruments may be used during a surgical procedure after the first shaft has been positioned in a subject's naturally occurring orifice. In some embodiments, a surgical instrument may be coupled to the first shaft. The surgical instrument may be coupled to the first shaft to ensure the stability of the surgical instrument relative to the first shaft and/or the subject. Portions (e.g., a distal end) of the surgical instrument may be positionable relative to the first shaft even when the surgical instrument is coupled to the first shaft. The surgical instrument may be coupled to the first shaft using any known method or system.

In some embodiments, the method may include observing a surgical site in the subject using an imaging device and a light source coupled to the first shaft. In some embodiments, the method may include conveying a fluid through a second shaft to a surgical site. The fluid may include saline. The fluid may be sterile to reduce the incidence of infections to the subject. The second shaft may be coupled to the first shaft. The method may include conveying a fluid through a third shaft from a surgical site. The third shaft may be coupled to the first shaft. In some embodiments, the second shaft and the first shaft may be the same shaft. In this embodiment the pressure applied to the second/third shaft is just reverse, for example, initially positive pressure is applied to the second/third shaft to convey fluids to and/or adjacent a surgical site, followed by applying negative pressure in order to remove fluids from and/or adjacent the surgical site.

Fluids may be applied in order to facilitate visualization of the surgical site for a user. Fluids may be applied in order to clean away unwanted material (e.g., biological) and/or debris. Materials which may be advantageous to remove may include human biological fluids adjacent the surgical site which are interfering with the users visualization of the surgical site. Materials which are removed may include debris resulting from the surgical procedure, for example, pieces of bone or tissue which have been purposefully and/or accidentally cut away from the subject. Materials may include man made materials, for example, introduced during the surgical procedure. In some embodiments, fluids may include pharmaceuticals which may be applied to the surgical site.

In some embodiments, at least a distal end of the first shaft is flexible. The distal end of the first shaft may be flexible to accommodate positioning at least a portion of the surgical instrument adjacent a surgical site in the subject. Initially, in some embodiments, a portion of the first shaft inserted in a naturally occurring orifice during use may be substantially straight in order to facilitate insertion through the orifice. FIGS. 1A-B depict a representation of an embodiment of portions of device 100, including a cross-section of a portion of the device, for performing a natural orifice surgical procedure wherein distal end 120 of first shaft 110 is substantially straight. Upon insertion of at least distal end 120 of first shaft 110 the distal end may be bent relative to longitudinal axis 130 of the first shaft. Distal end 120 of first shaft 110 may be bent in order to position the distal end adjacent to the surgical site such that the site is accessible. FIG. 2 depicts a representation of an embodiment of portions of device 100 for performing a natural orifice surgical procedure wherein flexible distal end 120 is bent at an angle. In some embodiments, distal end 120 may be positioned relative to the remaining first shaft 110 in a controlled manner by a user. Control system 140 operated by a user, during use, may adjust the position of distal end 120 of first shaft 110.

In some embodiments, at least a portion of distal end 120 of first shaft 110 may include slits 150 cut through the first shaft from an edge of the channel towards the center of the first shaft such that the distal end of the first shaft is flexible. In some embodiments, slits 150 may be positioned on opposing sides of first shaft 110. Slits 150 may be cut towards the center of first shaft 110 but end before reaching a center line 130 of the first shaft. In embodiments with opposing slits 150, slits cut short of the center of the first shaft ensures that the opposing slits do not intersect with one another, which would obviously result in severing first shaft 110.

In some embodiments, opening 160 may be coupled to an end of slit 150 as it terminates towards center 130 of first shaft 110. The openings may allow the slits to more easily open up when a force is applied to the distal end of the first shaft resulting in the distal end bending.

By adjusting the number, the shape, the orientation, and the positioning of a plurality of the slits in the first shaft, as well as the depth and width of the slits, one is able to control the degree to which a distal end of the first shaft will bend when a force is applied. Adjusting the size and shape of the openings coupled to the slits may also control the degree to which a distal end of the first shaft will bend when a force is applied.

FIG. 3 depicts a representation of an embodiment of device 200 for performing a natural orifice transluminal discectomy, a distal end of which is positioned in natural orifice 170 during a transvaginal procedure. In some embodiments, one or more portions of a surgical instrument positionable in first shaft 110 may include slits and/or openings similar to the slits and/or openings described as regards the first shaft herein. At least a distal portion of a surgical instrument may include slits and/or openings to allow and/or control flexibility of the portion of the surgical instrument (e.g., as depicted in FIG. 3).

Functional portion 210 of a surgical instrument may not include slits and/or openings such that the functional portion is not flexible to any appreciable extent (e.g., beyond the natural flexibility of the material from which the functional portion is formed). For example, functional portion 210 may include a rasp coupled to a distal end of device 200 may not be flexible; however, distal end 220 of the surgical instrument to which the rasp is coupled may be flexible. In the embodiment depicted in FIG. 3 a rasp coupled to the end of a surgical instrument is used to perform a discectomy removing at least a portion of an intervertebral disc between two vertebrae 230. Other functional portions of a surgical instrument may include a pituitary rongeur, a Kerrison rongeur, an osteotome, or a curette. In some embodiments, a functional portion may be couplable to an elongated member such that a single elongated member with flexible distal portion may be used to insert multiple different functional portions through a first shaft in a subject.

In some embodiments, a first shaft may include a control system coupled to the first shaft. The control system may function to control a flexible portion of the first shaft. The control system may control a flexible portion of the first shaft such that a user, during use, controls how much the flexible portion bends and/or to what degree it bends. Control system 140 (an embodiment of which is depicted in FIGS. 1-2) may be positioned at proximal end 180 of first shaft 110 such that a user may access the control system when the distal end of the first shaft is positioned in a subject.

In some embodiments, control system 140 may include elongated member 190. Elongated member 190 may extend from control system 140 positioned at proximal portion 180 of first shaft 110 to flexible distal portion 120 of the first shaft. At least a portion of the elongated member may be flexible. The control system when activated may apply a force to the distal end of the elongated member. As force is applied to the distal end of the flexible elongated member the distal end applies a force to the distal end of the first shaft. Applying force to distal end 120 of first shaft 110 forces slits 150a adjacent the distal end of the elongated member to "open up" such that the gap between the sides of the slit in the first shaft increases. Slits 150b on the opposing side of first shaft 110 opposite elongated member 190 may at the same time "close" such that the gap between the sides of the slit in the first shaft decreases. The simultaneous opening and closing of opposing slits in the first shaft results in the distal end of the first shaft bending. The extent or degree of the bend may be controlled by how much force is applied by the control system.

A control system may include any number of devices for applying a force to a distal end of the elongated member. In some embodiments, control system 140 may include gear mechanism 240. Gear mechanism 240 may include teeth 250a which mesh with teeth 250b formed in a surface of a proximal end of elongated member 190. Upon activation of the control system the gear wheel may rotate. The rotating gear wheel rotates the teeth on the gear wheel which engage the teeth of the elongated member conveying or repositioning the proximal end of the elongated member which applies a force to the distal end of the elongated member. In some embodiments, control system 140 may be activated by control knob 260 coupled to gear wheel 240 which a user turns during use. FIG. 1A depicts a representation of an embodiment of control system 140 in an inactivated state wherein a force is not being applied by the proximal end of elongated member 190 upon the distal end of the elongated member such that distal end 120 of first shaft 110 is substantially straight. FIG. 2 depicts a representation of an embodiment of control system 140 in an activated state wherein a force is being applied by the proximal end of elongated member 190 upon the distal end of the elongated member such that distal end 120 of first shaft 110 is substantially bent relative to the embodiment depicted in FIG. 1A.

In some embodiments, elongated member 190 may be positioned in fourth shaft 270. FIG. 1B depicts a representation of a cross-section of an embodiment of a portion of device 100 for performing a natural orifice surgical procedure wherein the distal end is substantially straight. The fourth shaft may be coupled to the first shaft. The fourth shaft may be coupled to an exterior surface of the first shaft. The fourth shaft may be coupled to the exterior of the first shaft such that the fourth shaft is positioned substantially orthogonally to at least some of the slits in the first shaft.

Figure 4B:
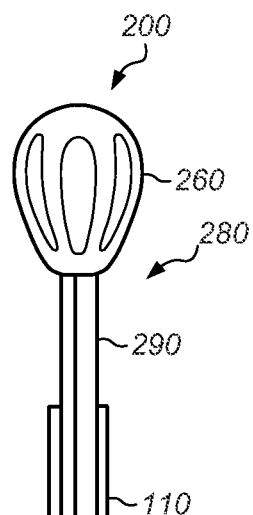
FIGS. 4A-C depict a representation of an embodiment of a device for performing a natural orifice transluminal discectomy.
Figure 4B:
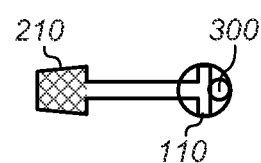
Figure 4C:
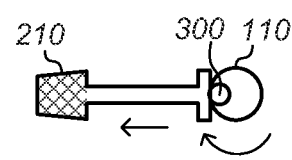
Figure 4A:
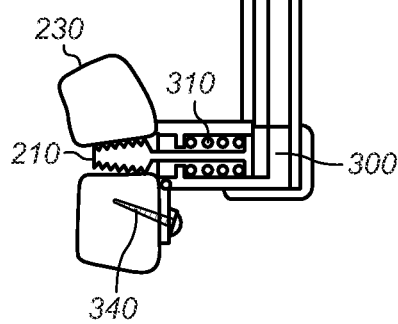

In some embodiments, a device (e.g., for performing a natural orifice transluminal discectomy) may function in a less complicated fashion during use. For example, device 200 depicted in FIG. 3 may be plunged repeatedly through first shaft 110 in order to use a rasp to perform a discectomy. In some embodiments, device 200 for performing a natural orifice transluminal discectomy, or similar spinal surgical instruments, may include a control system for operating functional portion 210 of a surgical instrument. FIGS. 4A-C depict a representation of an embodiment of device 200 with control system 280 for performing a natural orifice transluminal discectomy. Control system 280 may include a knob or handle 260 which is coupled to elongated member 290. Distal end 300 of elongated member 290 may be offset from a longitudinal axis of the elongated member. As a user activates control system 280 (e.g., by turning handle 260) distal end 300 may rotate around the longitudinal axis of the elongated member such that when rotated towards functional portion 210 it presses on a portion of the functional portion (e.g., depicted in FIG. 4C) pushing, during use, the functional portions out of first shaft 110 and in, for example, an intervertebral disc space (e.g., depicted in FIG. 4A). In some embodiment, control system 280 may include spring 310. When handle 260 is turned by a user pushing functional portion 210 out of first shaft 110, spring 310 may be compressed. When a user stops applying an active force to handle 260 compressed spring 310 may apply a force in an opposing direction pushing functional portion 210 back in first shaft 110 resetting distal end 300 (e.g., depicted in FIG. 4B).

In some embodiments, a surgical instrument may include a flexible distal end. In some embodiments, a degree of flexibility of the distal end may be limited by design (e.g., using slits and openings as described herein). In some embodiments, a surgical instrument may include a control system which allows a user to control a degree of bending of a flexible distal end of the surgical instrument. In some embodiments, a control system may not be necessary for a surgical instrument when a surgical instrument is positioned in a first shaft with a flexible distal and a control system for adjusting a degree of bending for the flexible distal end. The control system associated with the first shaft may adjust the degree of the bend of the distal end of the first shaft, which in turn will control an angle of approach of a flexible distal end of a surgical instrument inserted through the distal end of the flexed first shaft.

The first shaft may be formed from a variety of materials. A proximal portion may be formed from a first material and a distal portion may be formed from a second material. In some embodiments, at least a portion of the first shaft may be formed from stainless steel. One or more portions of a first shaft may be formed from one or more polymers.

In some embodiments, a first shaft may include outer sheath 320 (e.g., as depicted in FIG. 1A). The outer sheath may be formed from an elastomeric material. The first shaft may include an outer sheath to facilitate insertion of the first shaft in an opening such as a naturally occurring orifice in a human subject. The outer sheath may be formed from a material with a low coefficient of friction. In some embodiments, a coating may be applied to the outer surface of the outer sheath. A coating may reduce the coefficient of friction. Coatings may include active ingredients, for example, pharmaceuticals. Active ingredients may include antimicrobials in order to decrease incidents of infection during use.

In some embodiments, a first shaft may include an inner sheath. The inner sheath may be formed from an elastomeric material. The first shaft may include an inner sheath to facilitate insertion of, for example, surgical instruments, through the first shaft. The inner sheath may be formed from a material with a low coefficient of friction. In some embodiments, a coating may be applied to the outer surface of the inner sheath. A coating may reduce the coefficient of friction. Coatings may include active ingredients, for example, pharmaceuticals. Active ingredients may include antimicrobials in order to decrease incidents of infection during use.

In some embodiments, an inner and/or outer sheath may include a permanent sheath coupled to the first shaft. In some embodiments, an inner and/or outer sheath may include a disposable sheath positionable on at least a portion of the first shaft. Disposable sheaths may allow the first shaft to be reused.

Figure 5:
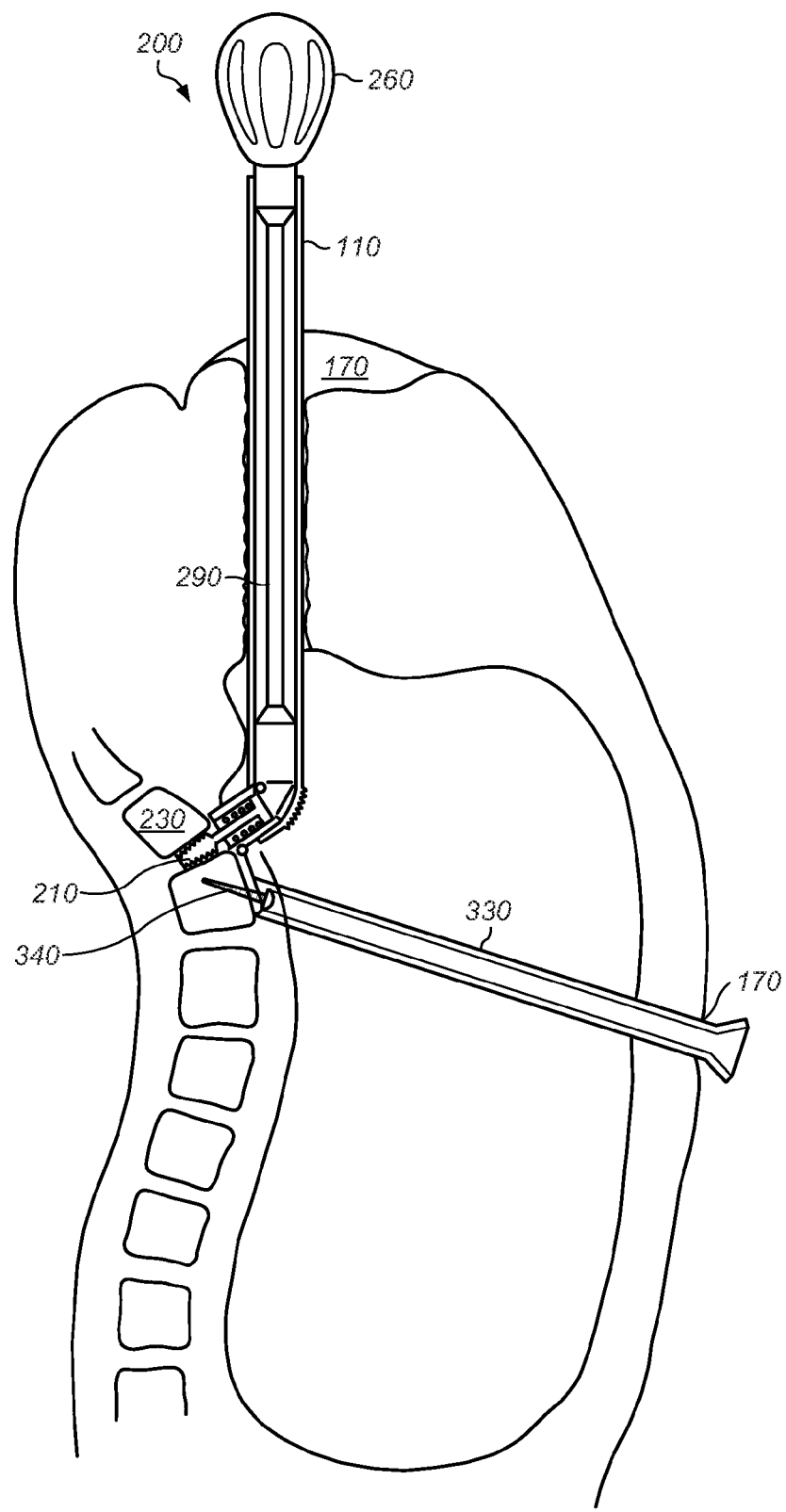
FIG. 5 depicts a representation of an embodiment of a device for performing a natural orifice transluminal discectomy, a distal end of which is positioned in a natural orifice during a transvaginal procedure. An embodiment is depicted of a secondary device for positioning a fastening device through an umbilical orifice to aid in transmitting forces with the primary device.

In some embodiments, a method may include securing a position of at least the distal end of the first shaft adjacent the surgical site in the subject relative to the surgical site. In some embodiments, the distal end of the first shaft may be directly coupled to a surgical site and/or adjacent to the surgical site. The distal end of the first shaft may be coupled directly to and/or adjacent the surgical site. In some embodiments, a distal end of the shaft may be coupled to a vertebrae with, for example, a screw. FIG. 5 depicts a representation of an embodiment of a first shaft 110 positioned in a subject during a transvaginal procedure. Device 200 for performing a transluminal discectomy is depicted in FIG. 5 positioned in first shaft 110. An embodiment through umbilical orifice 170 is depicted of device 330 for positioning fastening device 340 (e.g., a screw) or this cannula simply applies a force on the flange on the end of device 200 in order to hold it steady against the vertebra.

Figure 6:
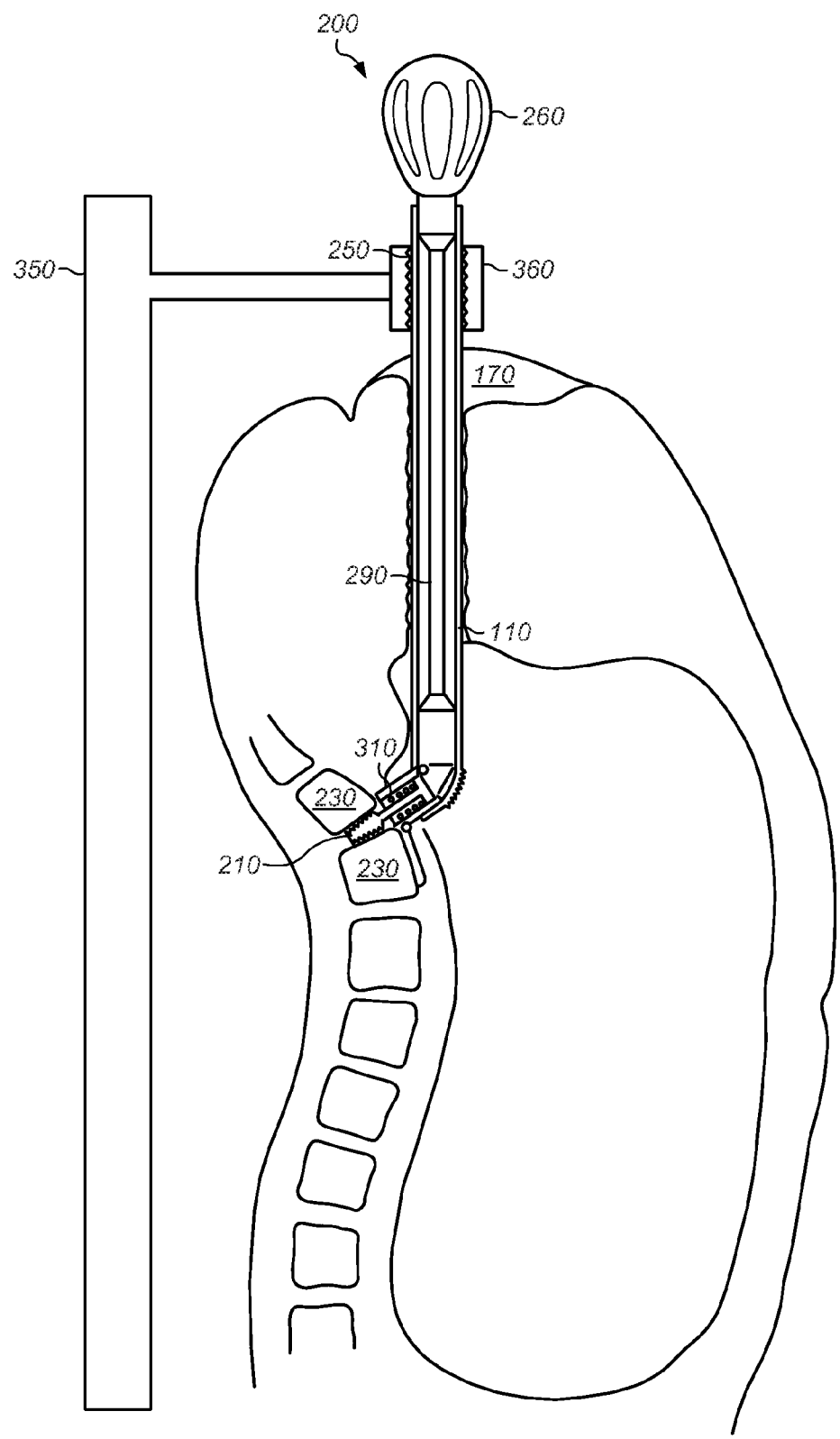
FIG. 6 depicts a representation of an embodiment of a device for performing a natural orifice transluminal discectomy, a distal end of which is positioned in a natural orifice during a transvaginal procedure.

A position of a first shaft and/or a surgical instrument may be secured relative to a surgical site. In some embodiments, first shaft 110 and/or a surgical instrument may be secured to operating table 350. FIG. 6 depicts a representation of an embodiment of device 200 for performing a natural orifice transluminal discectomy, a distal end of which is positioned in a natural orifice during a transvaginal procedure. First shaft 110 depicted in FIG. 6 is coupled to operating table 350 or held by an assistant. First shaft 110 depicted in FIG. 6 is coupled to operating table 350 with clamp 360. Coupling the outer shaft and/or surgical instruments to the operating table may provide more stability during use. In some embodiments, a subject of the surgical procedure may be coupled to the operating table such that the surgical site is inhibited from moving relative to the distal end of the outer shaft and/or the distal end of a surgical instrument.

In some embodiments, all or portions of a shaft may be flexible such that the shaft may be positionable in a naturally occurring orifice of a subject. In some embodiments, the shaft may be configured such that one or more of the flexible portions of the shaft may be stiffened upon activation by a user such that the portions are substantially rigid. In some embodiments, flexible portions may be made rigid upon activation by twisting a portion of the shaft. The flexible portions may be activated such that they are made rigid at such a time as a distal end of the shaft is positioned substantially adjacent a surgical site in the subject.

Making one or more flexible portions of the shaft substantially rigid may allow a user to gain the necessary leverage to perform the required surgical procedure. Certain spinal procedures may be particularly arduous because removing bone or other biologic tissue is difficult without direct longitudinal access. Currently rasps and/or a Kerrison rongeur may be employed to remove tissue; however as currently constructed both of these instruments may be inadequate for using in a flexible shaft. Herein new devices are presented which allow, for example, rasps and Kerrison rongeurs to be used in an at least partially flexible shaft. In some embodiments, a drill, burr, or other cutting device may be used to remove tissue material. A drill bit, burr, or other cutting device may be attached to a flexible elongated member which is manually operated to rotate the drill bit and/or coupled to a motor. Debris removal means (embodiments of which are described herein) may be used to remove bone and/or tissue displaced by the drill, burr or other cutting device.

In some embodiments, a spinal surgical procedure may include any known surgical procedure. In some embodiments, a spinal surgical procedure may include any known surgical procedure which may conceivably be carried out mostly through a naturally occurring orifice. In some embodiments, a spinal surgical procedure may include a fusion procedure. In some embodiments, a spinal surgical procedure may include a vertebralplasty procedure or a kyphoplasty procedure. A spinal surgical procedure may include coupling plates, screws, and/or rods to at least a portion of a spinal column. A spinal surgical procedure may include positioning interbody devices, bone cement (e.g., for vertebralplasty and Kyphoplasty) vertebral body replacement devices, disc replacement devices, nucleus devices, autografts, allografts, synthetic biological tissues, allograft tissue or other synthetic bone graft substitute material. In some embodiments, a spinal surgical procedure may include implanting one or more total disc replacements. A spinal surgical procedure may include administering pharmaceuticals. In some embodiments, a spinal surgical procedure may include a performing a corpectomy and/or implanting a corpectomy implant. Corpectomy implants may be used for replacing individual vertebrae or multiple segments of a subject's spine. In some embodiments, a spinal surgical procedure may include implanting one or more interspinous devices. In some embodiments, a spinal surgical procedure may include implanting one or more interprocesses devices. In some embodiments, a spinal surgical procedure may include implanting one or more bone plates and/or rods. Bone plates and/or rods may be used for fixing fractures or stabilizing spinal segments that a user (e.g., a surgeon) desires to fuse. In some embodiments, a spinal surgical procedure may include implanting one or more laminectomy implants. In some embodiments, a spinal surgical procedure may include implanting one or more inter-laminar fusion devices. In some embodiments, a spinal surgical procedure may include implanting one or more pedicle screws. In some embodiments, a spinal surgical procedure may include implanting one or more facet screws. In some embodiments, a spinal surgical procedure may include implanting one or more "stand-alone" interbody devices. Stand-alone devices may combine the spacer function of an interbody device with the fixation function of a plate. In some embodiments, a spinal surgical procedure may include implanting or positioning one or more discography injection materials. In some embodiments, a spinal surgical procedure may include implanting bone morphogenic proteins and/or other bone growth factors. In some embodiments, a spinal surgical procedure may include implanting cells. In some embodiments, a spinal surgical procedure may include implanting one or more tissue barriers or membranes. In some embodiments, a spinal surgical procedure may include implanting one or more platelet enriched plasma (PRP). In some embodiments, a spinal surgical procedure may include implanting one or more dural sealants. In some embodiments, a spinal surgical procedure may include implanting one or more electrical stimulators. In some embodiments, a spinal surgical procedure may include implanting one or more sacral-iliac fusion and/or reconstruction devices. In some embodiments, a spinal surgical procedure may include implanting one or more diagnostic devices. In some embodiments, a spinal surgical procedure may include a performing an annular repair and/or employing one or more annular repair devices including, but not limited to, surgical patches, meshes, sutures, suture anchors, adhesives etc. In some embodiments, a spinal surgical procedure may include implanting one or more sensors including, but not limited to, pressure sensors (e.g., for in vivo measurement on spinal growth plates). In some embodiments, a spinal surgical procedure may include implanting one or more pharmacological delivery systems used, for example, for delivering pharmaceuticals in vivo over a specified time period and/or after a delay. In some embodiments, a spinal surgical procedure may include nucleus replacement. In some embodiments, a spinal surgical procedure may include implanting one or more augmentation devices. In some embodiments, a spinal surgical procedure may include implanting at least one of all other conceivable spinal implants.

In some embodiments, a spinal surgical procedure may include a disc herniation repair procedure. A disc herniation repair procedure may include localizing a herniation; excising at least a portion of an expulsed disc material; and repairing the annulus.

In some embodiments, a spinal surgical procedure may include an anterior interbody fusion procedure conducted at least in part through a naturally occurring orifice. In some embodiments, a fusion procedure may be carried out anywhere along a spine, including but not limited to, within the lumbar and or cervical regions. The interbody fusion device may include stand alone fusion devices (e.g., including integrated screws) as well as zero or reduced profile fusion devices. In some embodiments, at least one of the naturally occurring orifices may include a vaginal orifice (e.g., as depicted in FIGS. 3 and 5-6). The spinal surgical procedure may include retracting tissue such that an intervertebral disc is more accessible. At least a portion of the spinal surgical procedure may include a discectomy. At least a portion of the spinal surgical procedure may include a discectomy wherein at least a portion of an intervertebral disc is removed.

At least a portion of the spinal surgical procedure may include distracting at least two vertebrae. At least a portion of the spinal surgical procedure may include distracting at least two vertebrae to increase a distance between at least two of the vertebrae. At least a portion of the spinal surgical procedure may include sizing an implant device.

At least a portion of the spinal surgical procedure may include implanting an interbody device. The interbody device may include an expandable interbody device. The expandable interbody device may include at least two portions which are assembled in the subject. At least two portions may be assembled in the subject such that the portions are smaller than the assembled expandable interbody device and as such easier to convey through the naturally occurring orifice of the subject. For a more in depth discussion of expandable interbody devices please refer to U.S. Patent Application to Tabor et al. filed on Nov. 17, 2011, entitled "EXPANDABLE INTERBODY DEVICE SYSTEM AND METHOD", which is incorporated fully herein by reference.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for performing spinal surgical procedures, comprising:
    positioning at least a portion of at least one surgical instrument in at least one naturally occurring orifice of a human subject by a user;
    accessing an interior space of the human using at least one of the surgical instruments;
    performing at least a portion of a spinal surgical procedure using at least one of the surgical instruments positioned in at least one of the naturally occurring orifices of the human; and
    removing at least one of the surgical instruments from at least one of the naturally occurring orifices prior to completion of at least a portion of the spinal surgical procedure.

2. The method of claim 1, further comprising positioning at least one second surgical instrument in at least a second naturally occurring orifice of the subject by the user.

3. The method of claim 1, further comprising positioning at least a distal end of a first shaft in at least one naturally occurring orifice, wherein at least a portion of at least one of the surgical instruments is positioned in the first shaft.

4. The method of claim 3, further comprising observing a surgical site in the subject using an imaging device coupled to the first shaft.

5. A method for performing an anterior interbody spinal fusion procedure, comprising:
    positioning at least a portion of at least one surgical instrument in at least one naturally occurring orifice of a human subject by a user, wherein at least one of the naturally occurring orifices comprises an umbilicus;
    accessing an interior space of the human using at least one of the surgical instruments;
    performing at least a portion of an anterior interbody spinal fusion procedure using at least one of the surgical instruments positioned in at least one of the naturally occurring orifices of the human; and
    removing at least one of the surgical instruments from at least one of the naturally occurring orifices prior to completion of at least a portion of the spinal surgical procedure.

6. The method of claim 5, further comprising positioning at least one second surgical instrument in at least a second naturally occurring orifice of the subject by the user.

7. The method of claim 5, further comprising visualizing a surgical site by the user using at least one of the surgical instruments.

8. The method of claim 5, further comprising removing tissue material using at least one of the surgical instruments comprising a cutting device.

9. The method of claim 5, further comprising retracting tissue such that a surgical site is more accessible by a user using at least one of the surgical instruments.

10. The method of claim 5, further comprising implanting an interbody device using at least one of the surgical instruments.

11. A device for assisting in the performance of a natural orifice transluminal spinal surgical procedure, comprising:
    a first shaft, wherein a distal end of a first shaft is positionable, during use, in at least one naturally occurring orifice, wherein the distal end of the first shaft is flexible to accommodate positioning the distal end of the first shaft adjacent a surgical site in the subject;
    a system which allows, during use, the flexible distal end to bend within predetermined limitations and/or directions; and
    at least one surgical instrument, at least a portion of which, is positionable, during use, in the first shaft, wherein at least one of the surgical instruments positions, during use, an expandable interbody device at the surgical site which is smaller than the expandable interbody device in its expanded state and, as such, is easier to convey through the naturally occurring orifice of the subject, and wherein at least one of the surgical instruments couples to a tool engagement feature of the expandable interbody device.

12. The device of claim 11, wherein at least one of the surgical instruments facilitates visualization, during use, of a surgical site by the user.

13. The device of claim 11, wherein at least one of the surgical instruments comprises a cutting device which facilitates removal of tissue material.

14. The device of claim 11, wherein at least one of the surgical instruments facilitates retracting, during use, tissue such that a surgical site is more accessible by a user.

15. The device of claim 11, wherein at least one of the surgical instruments facilitates implanting, during use, an interbody device.

16. The device of claim 11, wherein the first shaft comprises a fastener which secures, during use, a position of at least the distal end of the first shaft at least adjacent the surgical site in the subject.

17. The method of claim 1, further comprising visualizing a surgical site by the user using at least one of the surgical instruments.

18. The method of claim 1, further comprising removing tissue material using at least one of the surgical instruments comprising a cutting device.

19. The method of claim 1, further comprising retracting tissue such that a surgical site is more accessible by a user using at least one of the surgical instruments.

20. The method of claim 1, further comprising implanting an interbody device using at least one of the surgical instruments.

* * * * *